United States Patent [19]

Heller

[11] 4,388,822
[45] Jun. 21, 1983

[54] ATMOSPHERIC SAMPLING SYSTEM
[75] Inventor: Herbert Heller, Pittsburgh, Pa.
[73] Assignee: Mine Safety Appliances Company, Pittsburgh, Pa.
[21] Appl. No.: 283,537
[22] Filed: Jul. 15, 1981
[51] Int. Cl.³ .......................................... G01N 27/18
[52] U.S. Cl. ...................................... 73/23; 340/632
[58] Field of Search ................. 73/23, 27 R; 340/632, 340/633, 634; 422/96, 94, 98

[56] References Cited
U.S. PATENT DOCUMENTS 3,950,739 4/1976 Campman ........................... 340/634
4,073,194 2/1978 Willson et al. ........................... 73/23
4,314,475 2/1982 Karpov et al. ..................... 73/27 R Primary Examiner—Stephen A. Kreitman
Attorney, Agent, or Firm—Thomas H. Murray

[57] ABSTRACT

A three-wire digital atmospheric sampling system, particularly adapted to detect methane in mines, wherein accuracy is increased by ratiometric analog-to-digital conversion synchronized by a microprocessor. A reset signal, and read-out pulses indicative of the atmospheric condition, are transmitted along the same signal wire as are digital ratiometric signals, thus enabling the use of three conductors only between an atmospheric sampling probe, a microprocessor, and a visual read-out console.

6 Claims, 3 Drawing Figures

ATMOSPHERIC SAMPLING SYSTEM

BACKGROUND OF THE INVENTION

While not necessarily limited thereto, the present invention is particularly adapted for use with methane monitoring systems mounted on mining machines used in coal mines. The function of such a system is to detect the presence of methane, warn the operator of a potentially hazardous level, and to automatically cut off machine power in the event of an alarm condition. Originally, such systems were analog in nature and transmitted a signal, derived from a bridge containing the methane detector, back to read-out circuitry. Analog systems of this type, however, require frequent recalibration under difficult working conditions in a mine and cannot be calibrated unless the entire on-site system including interconnecting wiring is intact.

Subsequent systems converted the analog signal at the detector head into a digital signal which was transmitted back to the read-out via a single conductor. Such a system is described in a paper presented at the Fourth West Virginia University Conference on Coal Mine Electrotechnology, Aug. 4, 1978. In that system, however, digital read-out of gas concentration was not possible.

SUMMARY OF THE INVENTION

In accordance with the present invention, a new and improved atmospheric sampling system is provided which is digital in nature and wherein sensor-head analog-to-digital signal conversion is ratiometric and is synchronized by a remote microprocessor. Variations due to all but sensor chemical (i.e., gas) response and amplifier gain are effectively canceled out since the basic sensor and the amplifier are part of the sensing head. This is particularly advantageous in systems which must accommodate replacement precalibrated sensor assemblies without field adjustment or customization. The system also can accommodate a digital read-out and/or status indicator in contrast to prior art systems of this type.

Specifically, there is provided an atmospheric sampling system comprising sensor means for producing an electrical signal indicative of a particular gas content in the atmosphere, together with means for producing first electrical pulses of essentially constant width and means for producing second electrical pulses whose widths vary as a function of the gas content in the atmosphere. Additional means are provided for comparing the widths of the first and second pulses and for generating third pulses having a characteristic which varies as a function of the comparative widths of the first and second pulses. These third pulses are then applied to a visual status indication means.

In the embodiment of the invention shown herein, reset pulses generated by a microprocessor are applied to a common conductor along with the output of an analog-to-digital converter which produces serial digital signals, one of which is of essentially constant width and the other which has a width proportional to gas content. At the same time, depending upon the gas content, coded status signals are generated by the microprocessor and are applied, again, to the same common conductor and to light-emitting diodes which indicate status conditions such as normal, warning, alarm and trouble conditions.

The above and other objects and features of the invention will become apparent from the following detailed description taken in connection with the accompanying drawings which form a part of this specification, and in which.

Figure 1:
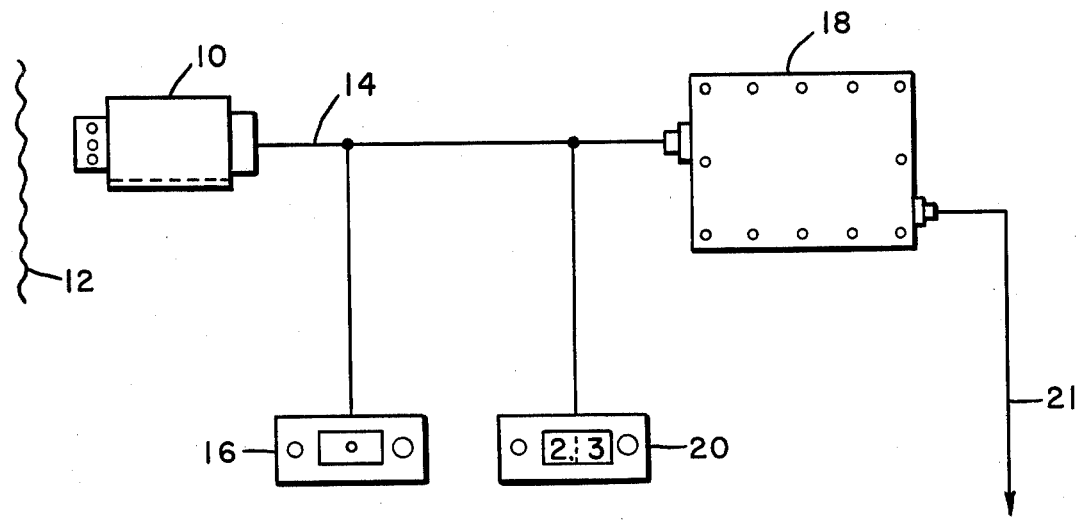
FIG. 1 is an illustration of the overall system of the invention showing the physical relationship between the sensor head, the microprocessor power supply and the indicating devices of the invention.

With reference now to the drawings, and particularly to FIG. 1, a methane sensor and its associated circuitry, hereinafter described, are contained within an enclosure 10 mounted on a mining machine closely adjacent the face area 12 being mined. The sensor apparatus is connected through a common three-wire cable 14 to a light-emitting diode status indicator 16 and to an explosion-proof box 18 which contains a microprocessor and other associated circuitry about to be described. Lead 21 is connected to a source of mine power.

A digital read-out 20 may also be connected across the three-wire cable and used in conjunction with the status indicator 16 or in lieu thereof.

Figure 2:
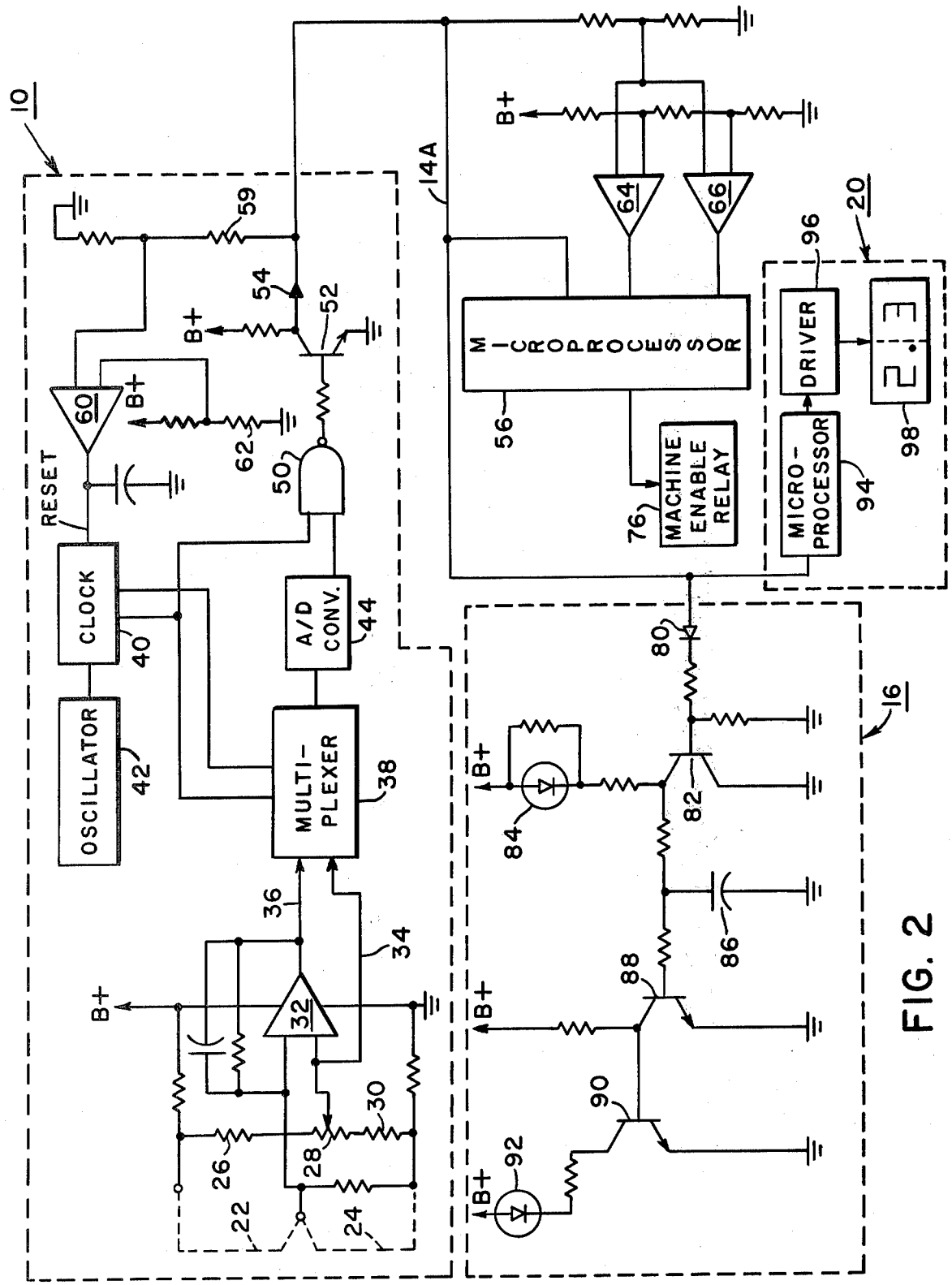
FIG. 2 is a more detailed schematic illustration of the system of the invention.

With specific reference to FIG. 2, the circuitry within the sensor 10 is enclosed by a broken line identified by the same reference numeral 10. The sensor itself comprises a bridge circuit including two legs containing gas-sensing elements 22 and 24 and a voltage divider comprised of resistors 26, 28 and 30. Resistor 28 is a potentiometer and has its movable tap connected to one input of an operational amplifier 32, the other input of the operational amplifier being connected to the midpoint between sensing elements 22 and 24. Potentiometer 28 is a zero-adjust potentiometer and is positioned when there is no methane or other gas present in the atmosphere (i.e., in known fresh air) such that the voltage on lead 34 is equal to the voltage on lead 36. When the bridge becomes unbalanced and responds to a change in atmospheric conditions, an output will appear from amplifier 32 on lead 36 such that the difference in voltage levels on leads 34 and 36 will be an analog indication of the methane or other gas content in the atmosphere. The signal is applied to a multiplexer 38 driven by a clock 40 and connected to an oscillator 42. The output of the multiplexer 38 is applied to an analog-to-digital converter 44 such that the output from the analog-to-digital converter will appear as serial pulses 46 and 48 (waveform A, FIG. 3). Pulse 46 is of constant width, but pulses 48 will vary in width depending upon the gas content sensed by the bridge sensor. If there is no methane present in the atmosphere, the width of the pulses 46 and 48 will be the same. However, as the gas content increases, the width of pulses 48 will decrease as shown by waveforms B and C in FIG. 3. These pulses are applied through NAND circuit 50, transistor amplifier 52 and diode 54 to the signal conductor 14A of the three-wire cable 14, also shown in FIG. 1. As will be appreciated, the three-wire cable 14 includes the signal conductor 14A as well as two power supply conductors, indicated as ground and B+ in FIG. 2, and connected to a power supply within the box 18 of FIG. 1.

Figure 3:
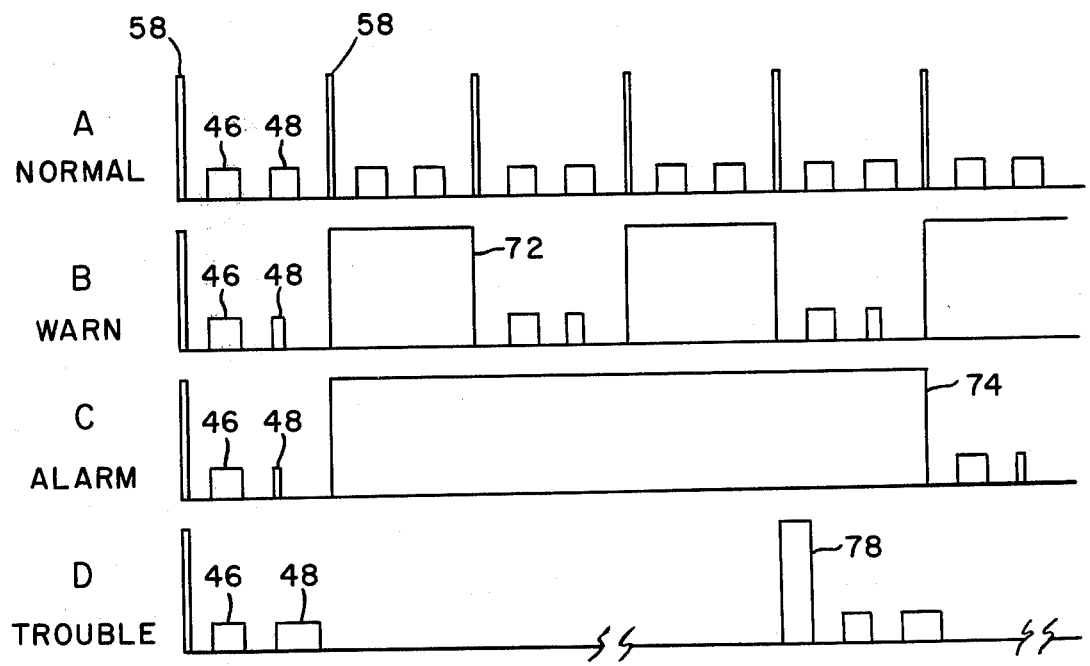
FIG. 3 comprises waveforms illustrating the operation of the invention.

Also carried within the box 18 is a master microprocessor 56 shown in FIG. 2 which generates reset pulses 58 (FIG. 3). These reset pulses are applied to the signal conductor 14A but are blocked by the diode 54.

They are, however, applied through a resistor 59 to an operational amplifier 60, the other input to the operational amplifier being connected to a voltage divider 62. In effect, the operational amplifier 68 compares the height of the pulses on signal conductor 14A with the bias voltage supplied from voltage divider 62. If the pulses on conductor 14A exceed a predetermined height, they are applied to the clock 40 to reset the same. Thus, the signal conductor 14A carries the reset pulses 58 generated by the master microprocessor 56 as well as the pulses 46 and 48 previously described. These latter pulses, however, do not pass through amplifier 60 since their amplitudes are too low to overcome the bias supplied by voltage divider 62.

The pulses 46 and 48 are applied to the microprocessor 56 through operational amplifier comparators 64 and 66 which block the reset pulses 58. Within the microprocessor 56, the widths of the pulses 46 and 48 are compared. If the width of pulse 48 is less than that of pulse 46, methane is present in the atmosphere. Additionally, the microprocessor 56 generates read-out pulses of varying widths, depending upon the methane content. For example, when the methane content reaches 1%, the microprocessor, by comparing the widths of pulses 46 and 48, generates relatively long pulses 72 (waveform B of FIG. 3) between successive reset pulses 58. When the methane content exceeds 2%, an alarm condition exists; and a long pulse 74 is applied to signal conductor 14A as illustrated by waveform C in FIG. 3, Additionally, when an alarm condition exists, the microprocessor 56 triggers a machine-enable relay 76 to shut down the mining machine. If the width of pulses 48 exceeds that of pulse 46, a condition equivalent to a negative or down-scale unbalance exists. If this condition exceeds a preset limit, a "trouble" condition is indicated by the generation of short pulses 78 illustrated in waveform D of FIG. 3. Pulses generated by the microprocessor 56 are applied through signal conductor 14A and diode 80 to circuitry within the indicator 16 of FIG. 1. This circuitry is enclosed by a broken line in FIG. 2, again identified by numeral 16 and includes a transistor 82 whose base is connected to diode 80 and which drives light-emitting diode 84. During normal operation and with the methane content below 1%, reset pulses 58 will periodically trigger the diode 84 in a characteristic fashion to indicate that normal conditions exist. These reset pulses will be shunted to ground by capacitor 86 and will not pass to transistors 88 and 90 to trigger a second light-emitting diode 92. However, when longer pulses are generated, such as pulses 72 and 74, these will pass through the transistors 88 and 90 and will trigger the light-emitting diode 92. Waveform B will cause the two diodes 84 and 92 to flash periodically; whereas waveform C will cause both the diodes 84 to remain ON for relatively long periods of time. A disabled condition is indicated by a flash once every 5 seconds as indicated by waveform D in FIG. 3.

The digital read-out 20 is enclosed by broken lines in FIG. 2 and identified by the same reference numeral. It includes a second microprocessor 94 which is identical to microprocessor 56 and includes operational amplifiers, not shown, similar to operational amplifiers 64 and 66 which feed pulses 46 and 48 into the microprocessor but block the reset pulses 58. The microprocessor 94, however, does not apply reset pulses to the conductor 14A. The microprocessor 94, in turn, is connected through a driver circuit 96 to a digital display assembly 98 which may, for example, be either a light-emitting diode display or a liquid-crystal display.

The present invention thus provides a fail-safe atmospheric sampling system which eliminates the complexities of custom-sensor wiring having parameters which directly affect system calibration. The digital system of the invention, interconnected by a common bus, is fail-safe for any combination of shorts, opens or intermittent connections. Furthermore, the system can accommodate precalibrated sensor assemblies. In coal mining operations, particularly, it is of advantage to install equipment on a go-no-go basis to avoid having the mining machine operator make on-operation calibrations with attendant error possibilities.

Although the invention has been shown in connection with a certain specific embodiment, it will be readily apparent to those skilled in the art that various changes in form and arrangement of parts may be made to suit requirements without departing from the spirit and scope of the invention.

I claim as my invention:

1. In an atmospheric sampling system, the combination of sensor means for producing an electrical signal indicative of a particular gas content in the atmosphere, means for producing first electrical pulses of essentially constant width, means for producing second electrical pulses whose widths vary as a function of said gas content in the atmosphere, means for comparing the widths of said first and second pulses, means for generating third pulses having a characteristic which varies as a function of the comparative widths of said first and second pulses, and indicator means actuated by said third pulses.

2. The system of claim 1 wherein said means for comparing the widths of said first and second pulses and for generating said third pulses comprises a microprocessor.

3. The system of claim 2 wherein said microprocessor, said indicator means and said means for producing first and second electrical pulses are connected to a common conductor on which all of said pulses appear.

4. The system of claim 1 wherein the characteristic of said third pulses which varies is the widths of said third pulses.

5. The system of claim 4 wherein said indicator means comprises light-emitting diode means.

6. The system of claim 1 wherein said means for comparing the widths of said first and second pulses comprises a microprocessor, and including digital read-out means connected to said microprocessor for indicating the difference in widths between said first and second pulses.

* * * * *